United States Patent
Clotfelter

[11] 4,033,182
[45] July 5, 1977

[54] METHOD FOR MEASURING BIAXIAL STRESS IN A BODY SUBJECTED TO STRESS INDUCING LOADS

[75] Inventor: Wayman N. Clotfelter, Huntsville, Ala.

[73] Assignee: The United States of America as represented by the Administrator of the National Aeronautics and Space Administration, Washington, D.C.

[22] Filed: June 28, 1976

[21] Appl. No.: 700,673

[52] U.S. Cl. ................................ 73/88 R; 73/67.7
[51] Int. Cl.² ...................................... G01L 1/00
[58] Field of Search ............. 73/67.7, 67.8 R, 88 R

[56] References Cited
UNITED STATES PATENTS 3,587,297  6/1971  Kammer ........................... 73/88 R
3,812,709  5/1974  Benson et al. ................. 73/67.8 R Primary Examiner—James J. Gill
Assistant Examiner—Anthony V. Ciarlante
Attorney, Agent, or Firm—L. D. Wofford, Jr.; J. H. Beumer; John R. Manning

[57] ABSTRACT

A method for measuring stress in test articles including the steps of obtaining for a calibrating specimen a series of transit time differentials between the second wave echo for a longitudinal wave and the first wave echo for each of a pair of shear waves propagated through the specimen as it is subjected to a known stress load of a series of stress loads for thus establishing a series of indications of the magnitudes for stress loads induced in the specimen, and thereafter obtaining a transit time differential between the second wave echo for a longitudinal wave and the first wave echo for each of a pair of shear waves propagated in the planes of the stress axes of a test article and comparing the transit time differential thus obtained to the series of transit time differentials obtained for the specimen to determine the magnitude of biaxial stress in the test article.

10 Claims, 4 Drawing Figures

| TENSILE STRESS KSI | TRANSIT TIME ORIENTATION "A" NANOSECS | DIFFERENTIAL ORIENTATION "A" NANOSECS / IN |
|---|---|---|
| 0 | 460.5 | 115.1 |
| 5 | 420.0 | 105.0 |
| 10 | 375.0 | 93.7 |
| 15 | 324.5 | 81.1 |
| 20 | 272.5 | 68.1 |
| 25 | 235.5 | 58.8 |

METHOD FOR MEASURING BIAXIAL STRESS IN A BODY SUBJECTED TO STRESS INDUCING LOADS

ORIGIN OF THE INVENTION

The invention described herein was made by an employee of the United States Government and may be manufactured or used by or for the Government for governmental purposes without the payment of any royalties thereon or therefor.

BACKGROUND OF THE INVENTION

1. Field of the Invention

The invention generally relates to a method for non-destructively measuring principal components of complex stress fields in a test article, and more particularly to an improved method for measuring stress ultrasonically.

2. Description of the Prior Art

The use of nondestructive methods based upon ultrasonic birefringence has been suggested for measuring stress level changes in laboratory specimens of anisotropic materials. However, only one component of three dimensional stress fields normally are obtainable through use of such methods. While the birefringence method tends to work reasonably well in uniform laboratory specimens, where only one principal stress axis exists, it is noted that stress is a complex force field and where two or more of the stress components are near the same magnitude, birefringent differentials may be near zero, particulary when large stress levels actually exists in a specimen.

Therefore, there currently exists a need for a practical nondestructive method for measuring orthogonal components of complex stress fields in test articles subjected to loading in non-laboratory environments.

It is, therefore, a general purpose of the instant invention to provide a nondestructive method of measuring sub-surface biaxial stress fields in engineering structures which is simple and economic to employ and overcomes the aforementioned disadvantages.

OBJECTS AND SUMMARY OF THE INVENTION

It is an object of the instant invention to provide a method for nondestuctively measuring biaxial stress which overcomes the aforementioned difficulties and disadvantages.

It is another object to provide a nondestructive method of measuring biaxial stress levels existing in engineering materials and structures.

It is another object to provide a nondestructive method of measuring sub-surface biaxial stress in a non-laboratory environment.

It is another object to provide a method of measuring biaxial stress in a body subjected to stress loading which includes the steps of measuring time differentials between ultrasonic shear waves and longitudinal waves propagated along parallel paths through the stress materials.

It is another object to provide a method wherein the time differential between the second wave echo for a longitudinal wave and the first wave echo for each of a pair of orthogonally related shear waves propagated through a test article is determined and compared to time differentials established between the second wave echo for a longitudinal wave and the first wave echo for each of a pair of orthogonally related shear waves propagated through a calibrating specimen of the same material, thermal conditioning, and grain orientation as the test specimen.

These and other objects and advantages are achieved through the use of a method wherein time differentials between ultrasonic shear waves and longitudinal waves propagated through a calibrating specimen are established to provide indications of stress in the specimen and thereafter time differentials are established between ultrasonic shear waves and longitudinal shear waves propagated through test articles and compared to the time differentials established to provide indications of stress, for thus determining the magnitude of stress in the test articles, as will hereinafter become more readily apparent by reference to the following description and claims in light of the accompanying drawings.

DESCRIPTION OF THE PREFERRED EMBODIMENT

The characteristics of ultrasonic waves are generally well understood. For example, it is known that the principal effect of stress on ultrasonic waves propagated through metallic materials occurs in the direction of material vibration or particle motion for the particles of the crystalline lattice of metallic materials. It is known, also, that X-cut crystals are suitable for use as transducers for propagating longitudinal waves to initiate vibration in the direction of propagation, while Y-cut crystals are suitable for use as transducers for propagating shear waves orthogonally related to the direction of propagation. For the sake of convenience, transducers employed in propagating longitudinal waves are hereinafter referred to as longitudinal wave transducers while transducers employed for propagating shear waves are hereinafter referred to as shear wave transducers.

It is also recognized by those familiar with the measurement of stress in metallic bodies employing ultrasonic waves that longitudinal waves propagated along paths normally related to planes of stress tend to be unaffected by the stress while the transit time for shear waves propagated along similar paths tends to increase as tensile stress increases and decreases as compressive stress increases. Therefore, since a shear wave transducer can be rotated 360°, it is possible to obtain transit time values indicative of sub-surface stress occuring along multiple stress axis by employing the transit time for the longitudinal waves as a reference and the transit time of the shear waves as stress indications.

Hence, the determination of magnitudes of stress ultrasonically is essentially a measurement of ultrasonic velocity through the material of a test article. The following expression depicts this velocity/stress relationship.

$$\Delta V(s) = \frac{-T(4u + n)}{8u\,V_p}$$

Where: V = Velocity
 −T = Compressive Stress
 u = Second Order Elastic Constant
 n = Third Order Elastic Constant
 p = Density
 s = Shear Waves In addition to stress, numerous material properties affect velocity of sound in a medium. Fortunately, the effects of these variations can be accounted for by adequate calibration.

Figure 1:
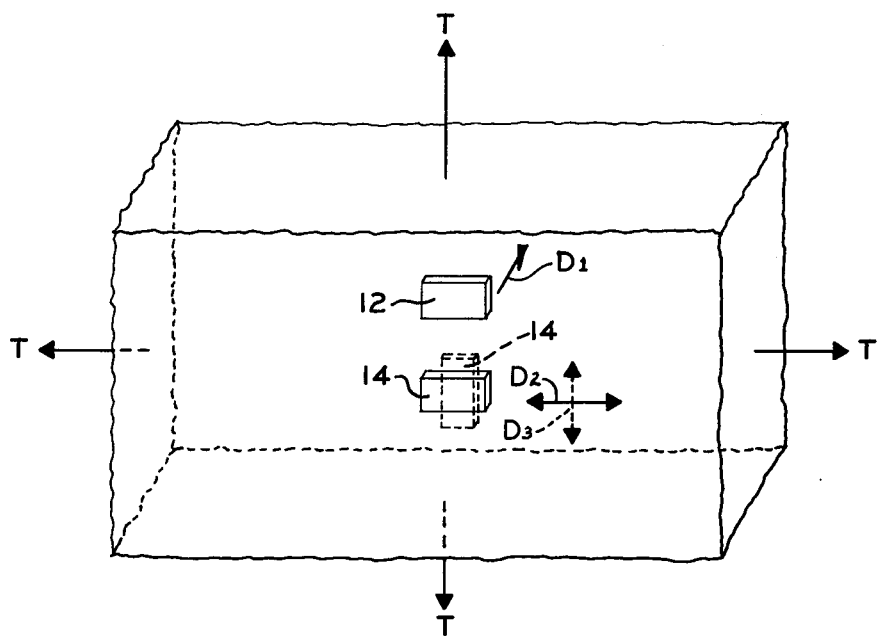
FIG. 1 is a diagrammatic view illustrating a calibrating specimen subjected to tensile stress to be measured in accordance with the method which embodies the principles of the instant invention employing longitudinal and shear wave transducers attached thereto.
Figures 3, 4:
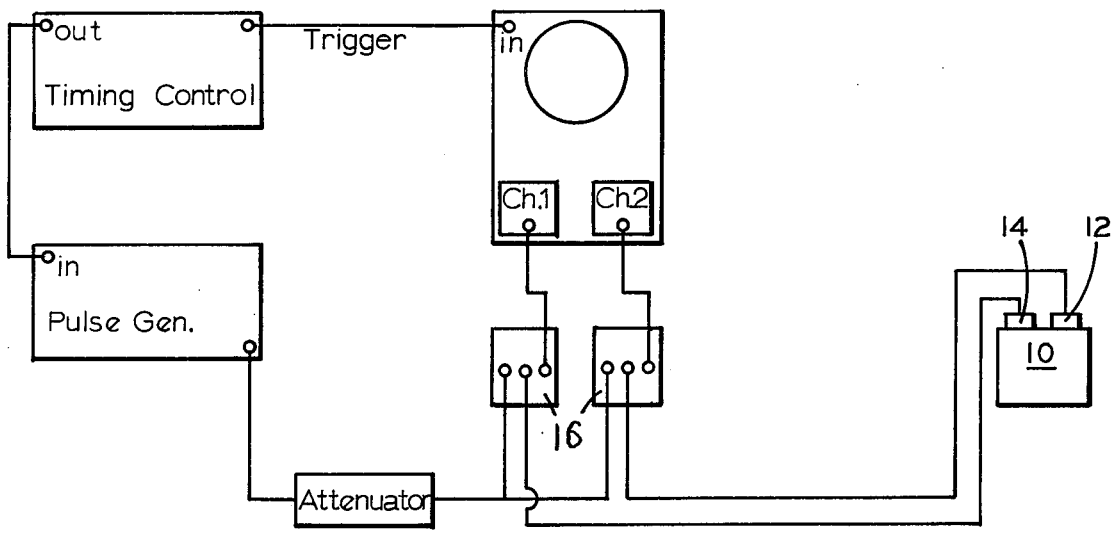
FIG. 3 is a table depicting a typical compilation of data prior to plotting on the graph illustrated in FIG. 2.
FIG. 4 is a diagrammatic view illustrating oscilloscope circuitry which may be employed in performing the method of the instant invention.

As illustrated in FIGS. 1 and 4 of the drawings, a calibration specimen, designated 10, FIG. 4 may be subjected to tensile stress along orthogonally related axes, while a longitudinal wave transducer 12 is attached to the body for propagating longitudinal waves along a path normal to the planes of the stress while a shear wave transducer 14 is attached thereto for propagating shear waves along paths paralleling the paths of the longitudinal waves. Of course, the particle motion induced by the longitudinal wave transducer 12 is in the direction of wave propagation, while the particle motion induced by the shear wave transducer 14, for each orientation thereof, is in a direction normal to the direction of wave propagation, as indicated by the directional arrows $D_1$, $D_2$ and $D_3$ of FIG. 1.

As illustrated in FIG. 4, where desired, the transducers 12 and 14 are connected in separate channels of a suitable dual beam oscilloscope, at diode switches 16. The time base of the oscilloscope is, in operation, expanded until each cycle of the narrow pulses can be observed visually. The distance or time between corresponding peaks of the two signals utilized as indicators is proportional to the stress in the specimen.

Since the circuitry of the oscilloscope forms no part of the instant invention and the design, purpose and modes of operation are well known, a more detailed description of the circuit is omitted in the interest of brevity. However, it should be appreciated that the instant invention embodies the concept of measuring time differentials between ultrasonic shear waves and longitudinal waves propagated through a stressed material along parallel paths, as indicated on the screen of the oscilloscope.

The indication obtained for the transit time of longitudinal waves propagated through a stressed material is suitable for use as a reference indication, while the transit time indication for shear waves are suitable to be employed as indications of stress.

The velocity of longitudinal waves in aluminum is approximately $2.46 \times 10^5$ cm/sec. while the velocity for shear waves is $1.22 \times 10^5$ cm/sec. Thus the transit time for the second wave echo for the longitudinal wave is of the same order of magnitude as the time required for the initial shear wave echo. This relationship provides a time differential small enough to be measured with high accuracy and substantially eliminates the need for highly accurate material thickness measurements. Of course, since the shear wave transducer 14 is capable of being reoriented to 90°, with respect to its initial orientation, it is possible to achieve a transit time measurement for the shear wave echos as particle motion is induced along orthogonally related planes of the stress axes for thus providing biaxial sensing of stress components.

In order to perform the method embodying the instant invention, a calibrating specimen having the same characteristics of the article to be tested is selected. Viz, a specimen is acquired from the same material as the test article, having the same thermal conditioning and the same grain orientation with respect to the accessible surface as the test article is used for calibration purposes.

Figure 2:
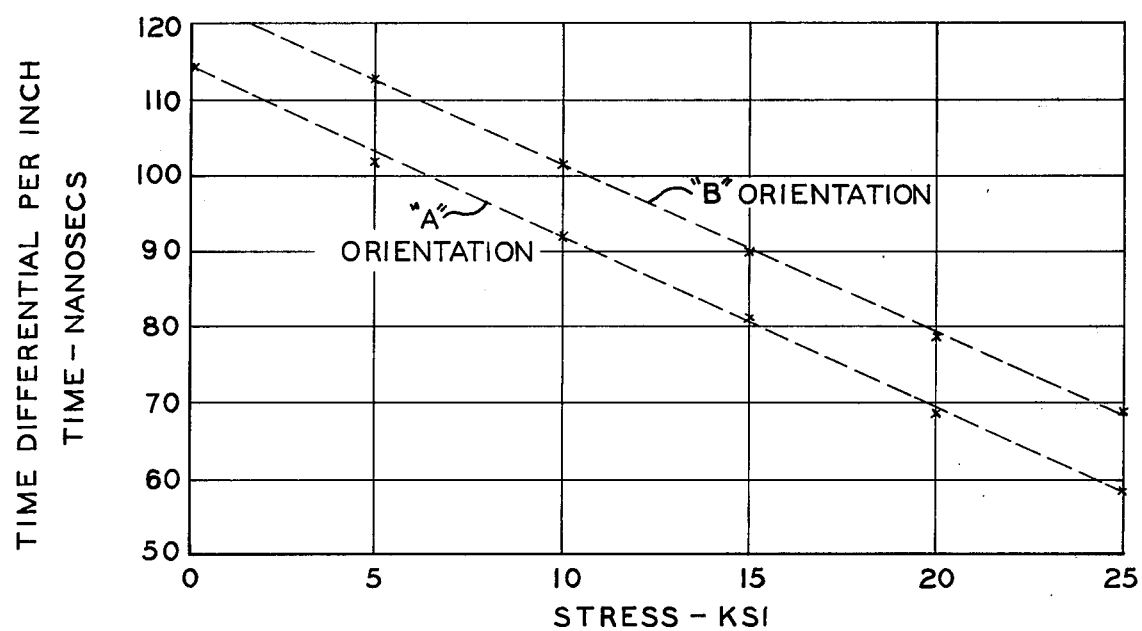
FIG. 2 is a graphic view depicting a series of transit time differentials for first wave echos for ultrasonic shear waves and second wave echos for longitudinal waves propagated through the specimen shown in FIG. 1, with alternate orientations of the shear wave transducer being employed.

As depicted in FIG. 3, data is compiled for a first orientation for the shear wave transducer 14, indicated ORIENTATION "A", FIG. 2, as the specimen is incrementally loaded. Similarly, data is compiled for the alternate orientation of the transducer 14, indicated ORIENTATION "B", FIG. 2.

With a zero load on the specimen, a measurement of the time differential between the second wave echo for the longitudinal wave and the first wave echo for the shear wave for each biaxial orientation of the transducer is made. The time differential is then converted to nanoseconds/inch and plotted on the graph of FIG. 2. For example, where the time differential between the first wave echo of the shear waves and the second wave echo for the longitudinal wave is 460.5 and the total length of the path along which the wave is propagated and reflected is 4 inches, the time differential is divided by the total length of the path to provide the time differential in terms of distance, or 115.1. The measurement is repeated for each load as the test specimen is incrementally loaded, in a uniform manner, through five increments. The data thus obtained, shown in FIG. 3, is plotted as shown in FIG. 2.

The shear wave transducer 12 is then rotated through 90° to ORIENTATION "B" and the calibrating process repeated for obtaining and compiling the data for the alternate orientation, as aforementioned. This data is then plotted, for ORIENTATION "B", as illustrated in FIG. 2.

Where desired, the time differential between the second longitudinal wave echo and the shear echo of each biaxial orientation of the transducer for an annealed calibration specimen is measured in order to indirectly measure the low level of residual stress existing in the calibration specimen and adjusting the stress values of the calibration specimen accordingly.

Measurement of stress in a test article is achieved by employing a longitudinal wave transducer and a shear wave transducer for obtaining time differential values between the second wave echo for longitudinal wave and the first wave echo for shear wave propagated by the transducer 14 at two orientations, namely, ORIENTATION "A" and ORIENTATION "B". The value of the time differentials thus acquired are compared to the data plotted on the graph of FIG. 2 for purpose of determining the magnitude of sub-surface stress along stress axes paralleling the direction of particle motion for the shear wave at each orientation of the transducer 14.

In summary, the method of the instant invention is performed by serially subjecting a calibration specimen to a series of incrementally increased loads of known magnitudes; obtaining the time differential between the transit time for the second wave echo for longitudinal wave ultrasonically propagated through the calibration specimen along a given path by longitudinal wave transducer as the specimen is subjected to each stress load and the transit time for the first wave echo for each of a pair of shear waves propagated in orthogonal planes ultrasonically along a path paralleling said given path by a shear wave transducer vibrating the particles of the crystalline lattice of the body in parallelism with the stress axes extended through the calibration specimen as the specimen is subjected to each stress load; obtaining two series of transit time differential values and dividing the transit time differential values by the total length of the paths traversed by the ultrasonic waves for thus establishing a series of stress values for ORIENTATION "A" and ORIENTATION "B" for the transducer 14; obtaining a first transit time differential value between the second wave echo for longitudinal wave propagated along a first path through a test specimen, such as the wall of a pressure vessel subjected to unknown stress, and a first wave echo for a shear wave propagated, by a shear wave transducer in an orientation corresponding to ORIENTATION "A", along a second path extended through the specimen paralleling the first path for vibrating the crystalline lattice thereof in parallelism with the first stress axis for the test specimen; comparing the transit time differential value obtained for the test specimen to the series of stress values for ORIENTATION "A" for determining the magnitude of stress occuring along the first stress axis of the test specimen; rotating the shear wave transducer 14 through 90° and obtaining a second transit time differential between the second wave echo for a longitudinal wave propagated through the test specimen and a first wave echo for a shear wave propagated through the test specimen by the transducer in an orientation corresponding to ORIENTATION "B" for vibrating the crystalline lattice in parallelism with a second stress axis; and comparing the second transit time differential valve thus obtained for the test specimen to the second series of stress values for ORIENTATION "B" for thus determining the magnitude of stress occurring along the second stress axis of the specimen.

In view of the foregoing, it should readily be apparent that the method of the instant invention comprises a practical, nondestructive method for ultrasonically measuring stress in test articles such as engineering structure and the like.

Although the invention has been shown and described in what is conceived to be the most practical and preferred method, it is recognized that departures may be made therefrom within the scope of the invention, which is not to be limited to the illustrative details disclosed.

I claim:

1. In a method for ultrasonically measuring stress in a test article, the steps comprising:
   A. obtaining a transit time differential between the second wave echo for a longitudinal wave propagated along a first path through a stressed test article and the first wave echo for at least one shear wave propagated through the article along a second path paralleling said first path; and
   B. comparing the obtained transit time differential to an established transit time differential indicative of a measurement of stress.

2. The method of claim 1 wherein said established transit time differential is established by a method including the steps of:

obtaining a transit time differential between the second wave echo for a longitudinal wave propagated along a given path through a specimen having the characteristics of said test article and subjected to stress of a known magnitude and the first wave echo for a shear wave propagated through the specimen, along a path paralleling said given path.

3. The method of claim 2 wherein the transit time differential is established by the further step of dividing the transit time differential by the total length of the given path through the specimen and plotting on an X-Y graph the thus obtained value against the known value of stress.

4. The method of claim 1 wherein said established transit time differential is established by a method including the steps of:
   A. incrementally subjecting a specimen having the characteristics of said article to a series of stress loads of known magnitudes;
   B. electronically establishing a first series of transit time indications for the second wave echo for longitudinal waves propagated by a longitudinal wave transducer through the specimen as it is subjected to each stress load of the series of stress loads;
   C. electronically establishing a second series of transit time indications for the first wave echo for shear waves propagated by a shear wave transducer through the specimen as the specimen is subjected to each stress load of the series of stress loads;
   D. comparing the electronically established transit time indications of said first and second series for obtaining a first series of transit time differentials indicative of a measurement of stress; and
   E. dividing each transit time differential of the series by the total length of the waves through the specimen.

5. The method of claim 4 wherein the step of obtaining a transit time differential for a stressed test article includes the steps of:
   A. electronically establishing a first transit time indication for the second wave echo for a series of longitudinal waves propagated by a longitudinal wave transducer through the test article along said first path;
   B. electronically establishing a second transit time indication for the first wave echo for a series of shear waves propagated in the plane of a first stress axis along said second path through the test article for obtaining a second transit time; and
   C. comparing the established first and said second transit time indications.

6. In method of claim 5 the further steps of:
   A. electronically establishing the transit time indication for the first shear wave echo for another series of shear waves propagated in the plane of a second stress axis angularly related to the plane of the first stress axis along said second path through the test article for thus obtaining a further second transit time indication;
   B. comparing said first and said further transit time indications for obtaining another transit time differential, whereby the magnitude of stress along the second stress axis is detected; and
   C. comparing the other transit time differential to another established transit time differential indicative of a measurement of stress.

7. The method of claim 6 wherein said other established transit time differential is established by a method including the steps of:
   determining the transit time differential between the second wave echo for a longitudinal wave propagated along the given path through the specimen as it is subjected to stress of a known magnitude and the first wave echo for a shear wave propagated through said specimen in the plane of a second stress axis.

8. The method of claim 6 wherein the other established transit time differential is established by a method including the steps of:
   A. incrementally subjecting the specimen to a series of stress loads of known magnitudes;
   B. electronically establishing a third series of transit time indications for the second wave echo for longitudinal waves propagated by a longitudinal wave transducer through the specimen as it is subjected to each stress load of the series of stress loads;
   C. electronically establishing a fourth series of transit time indications for the first wave echo for shear waves propagated by a shear wave transducer through the specimen as the specimen is subjected to each stress load of the series of stress loads;
   D. comparing the electronically established transit time indications of said first and second series for obtaining another series of transit time differentials; and
   E. dividing each transit differential of the other series of transit time differentials by the total length of the wave path through the specimen.

9. A method for determining the magnitude of biaxial stress in matallic test articles, comprising the steps of:
   A. serially subjecting a specimen having characteristics similar to the characteristics of an article to be tested to a series of incrementally increased stress loads of known magnitudes, electronically establishing a transit time indication for the second wave echo for a longitudinal wave propagated through the specimen along a given path as the specimen is subjected to each load of the series for thus obtaining a first series of first transit time indications;
   B. electronically establishing a transit time indication for the first wave echo for each of a pair of orthogonally related shear waves propagated along paths paralleling said given path through said specimen for vibrating particles of the crystalline lattice thereof in the planes of a first and a second orthogonally related stress axis extended through the specimen as the specimen is subjected to each stress load of the series of known stress loads for thus obtaining a second and a third series of transit time indications;
   C. comparing the indications of said first series of transit time indications with the indications of said second and third transit time indications for obtaining a first and a second series of transit time differentials, and dividing each of the transit time differentials by the total length of the paths through the specimen, for thus establishing a series of time differential values indicative of stress magnitude for the orthogonally related stress axes for said specimen;
   D. obtaining a pair of transit time differential indications between the second wave echo for a longitudinal wave propagated along a first path through a test article subjected to an unknown stress and the first wave echo for each shear wave of a pair of shear waves propagated along a second path extended through the test article paralleling said first path for vibrating the crystalline lattice thereof in the planes of a first and a second stress axis for said test specimen; and
   E. comparing said pair of transit time differential values obtained for the test article to the series of time differential values established for the specimen for thus determining the magnitude of stress occurring along the first and second stress axes of the test article.

10. In a nondestructive method for measuring stress in a test article ultrasonically, the steps comprising:
   obtaining transit time differentials between the second wave echo for a longitudinal wave and the first wave echo for each shear wave of a pair of shear waves propagated in the planes of angularly related stress axes along paths paralleling the path of the longitudinal wave through a test article and comparing the transit time differentials for thus obtaining a pair of transit time differentials indicative of measurements of stress along said axes.

* * * * *